United States Patent [19]
McCullough

[11] Patent Number: 4,546,761
[45] Date of Patent: Oct. 15, 1985

[54] LARGE ANIMAL SPECULUM HOLDER AND BATTERY-POWERED ILLUMINATOR

[75] Inventor: Robert J. McCullough, Barrington, Ill.

[73] Assignee: McCullough Cartwright Pharmaceutical Corp., Barrington, Ill.

[21] Appl. No.: 457,434

[22] Filed: Jan. 12, 1983

[51] Int. Cl.⁴ .............................................. A61B 1/06
[52] U.S. Cl. ........................................ 128/6; 362/109
[58] Field of Search ..................... 128/3, 4, 5, 6, 7, 8, 128/10, 11; 362/109

[56] References Cited

U.S. PATENT DOCUMENTS

| | | | |
|---|---|---|---|
| 951,285 | 3/1910 | Meyer | 128/6 |
| 1,422,490 | 7/1922 | Stader | 128/6 X |
| 1,556,355 | 10/1925 | Roney | 128/6 |
| 1,635,822 | 7/1927 | Zeng | 128/6 |
| 2,469,857 | 5/1949 | Allyn | 128/6 X |
| 2,668,528 | 2/1954 | Frick | 128/3 |
| 3,631,852 | 1/1972 | Hay et al. | 128/3 |

*Primary Examiner*—William H. Grieb
*Attorney, Agent, or Firm*—McCaleb, Lucas & Brugman

[57] ABSTRACT

A speculum holder and illuminator comprises a handle containing battery and switch compartments separated by a sealed wall. A speculum support sleeve extends across the top and has a forward recess to hold a tubular speculum, and a viewing opening at the rear. A lighting assembly in the sleeve projects light forwardly in the speculum and is powered by a battery in the battery compartment connected through a switch in the switch compartment. An alternate form has a spring clip for temporarily holding it in a tubular speculum. A conductor card extends to a battery pack on the user's belt where it is supported on a crank-wound reel enabling it to be extended and retracted as needed.

11 Claims, 7 Drawing Figures

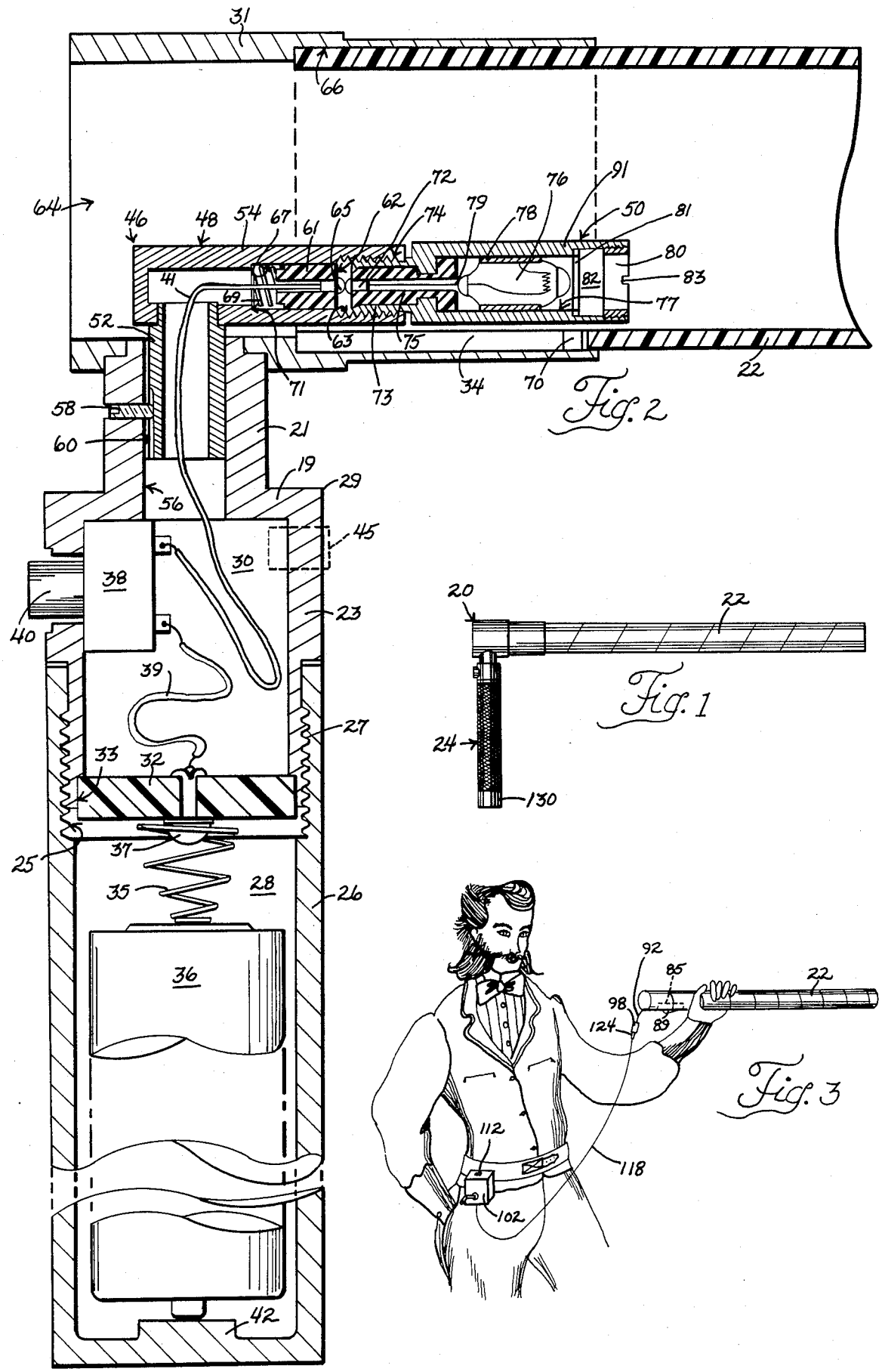

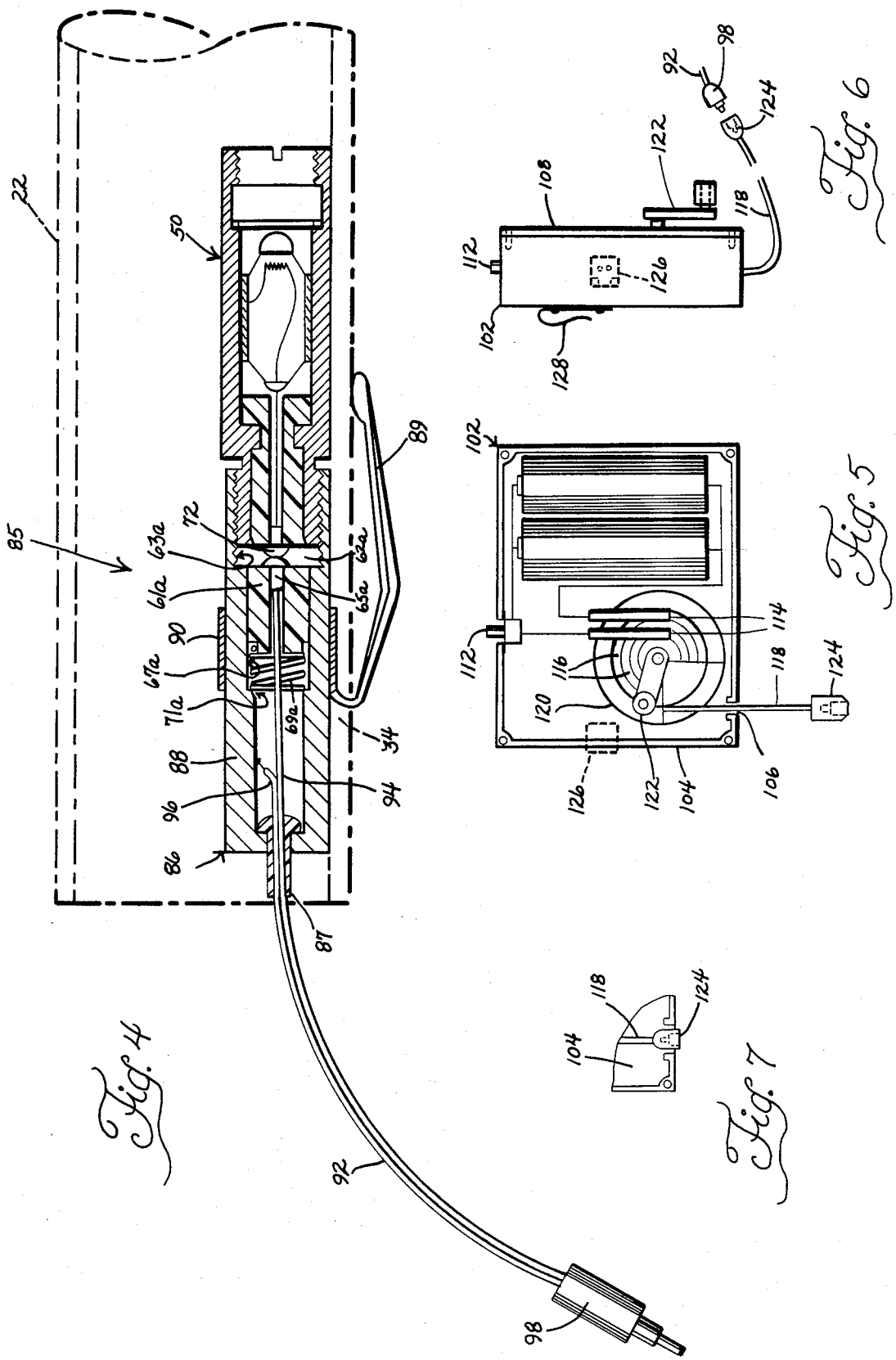

LARGE ANIMAL SPECULUM HOLDER AND BATTERY-POWERED ILLUMINATOR

BACKGROUND OF THE INVENTION

This invention relates to speculums, and more particularly to a speculum holder-illuminator to be used with sterile disposable or reusable speculum tubes for large animals.

Speculums are well known devices which are used in the medical examination of humans and animals by their insertion into natural body orifices in order to enable exposure of internal tissue structures for diagnostic or therapeutic purposes. They are conventionally used with a supplementary source of illumination in order that the tissue structures exposed and examined may be adequately inspected and evaluated.

In veterinary medicine, examination of horses and cows, for example, is often accomplished under less-than-optimum field conditions. This would be benefited significantly by the use of a sturdy, conveniently sized, corrosion resistant, easily disinfected speculum holder-illuminator with a self-contained high-intensity light source and a low weight, low volume power source. For best results, the speculum holder-illuminator must fasten into and become an integral unit with the speculum itself (which is routinely available as a sterile disposable or reusable plastic or coated cardboard tube) in order that the examiner may conveniently use the speculum holder to illuminate while adjusting the position of the distal speculum orifice to facilitate the manipulation and examination of internal tissues.

Since most diagnostic decisions are based upon color, texture and form of the tissues observed, the speculum holder-illuminator must have a light source and power supply which will provide a constant high-intensity illumination with a color temperature most like sunlight over the useful life of the light source and power supply. Under field conditions, the power supply and bulb life must be sufficient to enable uninterrupted use of the instrument throughout a working day. Replacement of the power source and bulb must be easily carried out under field conditions if necessary.

Diagnostic procedures often require specific testing of tissues observed at the distal end of the speculum. This may include sampling for histologic or pathologic examination or for microbiological or chemical analysis. Therapeutic or surgical procedures may require application of medications or other substances or materials. To that end, the speculum holder-illuminator unit must permit the free and unencumbered passage of a variety of veterinary instruments or appliances with minimal obstruction of view and maximum illumination intensity at the distal end of the speculum tube.

Further, the high-intensity light source must be protected to prevent direct fluid contact with the bulb. It may also be anticipated that fluid will enter the housing of the speculum holder, so all electrical connections must be sealed against fluid invasion. Such protection is needed because frequent cleaning and disinfection of the instrument will be required in normal use.

SUMMARY OF THE INVENTION

A principal object of the present invention is to provide a sturdily constructed speculum holder and battery-powered illuminator which will fasten to and become an integral unit with sterile disposable or reusable speculum tubes to enable veterinary type vaginal and cervical examination of large animals under field conditions.

One object of the invention is to provide a holder-illuminator which is completely self-contained and which, when connected to a speculum tube will permit continuous illumination of tissues and structures during the manipulation of the distal end to displace tissues or structures of interest. Manipulation of the distal end of the speculum tube while the tissues are illuminated may be accomplished with one hand free to insert diagnostic or therapeutic instruments through and guided by the lighted speculum tube.

Another object of the invention is to provide a speculum holder-illuminator which will be corrosion resistant, easily cleaned and disinfected or sterilized, and which will remain unaffected by the variety of liquids which are commonly used in veterinary medicine or which may be of biologic origin and which may come into contact with the speculum holder-illuminator.

Another object of the invention is to provide a sturdy and well protected source of constant high-intensity illumination by the use of a sub-miniature halogen cycle lamp encased and sealed into a metal housing with a protective front lens which will illuminate the tissues under observation with light of a color temperature most like sunlight in order to provide the veterinarian with constant and unaltered tissue appearances to facilitate diagnostice judgments.

Another object of the invention is to provide a rechargeable battery power source in the form of a battery stick which can be housed in a conveniently sized protected enclosure which will serve as the handle of the device and which will provide the needed voltage levels and ampere-hour capacity sufficient for the daily activities of the average large animal veterinarian. Further, the rechargeable battery and bulb housing may be easily replaced under field conditions, if necessary.

Another object of the invention is to provide a large proximal orificed speculum holder-illuminator which can allow for uninterrupted illumination of tissues while a variety of veterinary instruments and appliances are passed through the proximal end of the speculum holder-illuminator and into the speculum tube itself to accomplish the variety of diagnostic or therapeutic procedures common to veterinary medicine.

Another object of the invention is to provide a special tubular base bulb holder unit into which the protected bulb housing may be fitted to form a very light weight, compact speculum clip-illuminator, which may be temporarily fastened inside the proximal end of a sterile disposable or reusable speculum tube, thereby providing a constant source of high-intensity illumination without obstructing view through the proximal speculum end and enabling free passage of an instrument or appliance. Such clip-illuminator is easily disinfected or sterilized and when connected to a remote, belt-supported, auxiliary battery power source of ample capacity, can supply a substantial ampere-hour capacity enabling extended field operations which may include, for example, such activities as artificial insemination. The speculum clip-illuminator, as a fully sterilized unit, may optionally be inserted deep into the speculum tube to intensify illumination for surgical procedures without fear of contamination.

Another object of the invention is to provide a remote battery power pack in which a power cord is wound on a crank-operated reel within a casing and the reel is rotatable in one direction to pay out the cord for use and rotatable in the opposite direction to store it in the casing when not in use.

BRIEF DESCRIPTION OF THE DRAWINGS

Other objects and advantages will be apparent from the following description taken in connection with the accompanying drawings in which:

FIG. 1 is a side view of a self-powered speculum holder-illuminator illustrating one embodiment of the invention;

FIG. 2 is an enlarged fragmentary partially cross-sectional view of FIG. 1;

FIG. 3 is a view of an alterna.te embodiment showing a light weight version of the invention, namely a clip-illuminator, powered by a remote battery pack supported on the belt of a user;

FIG. 4 is a fragmentary longitudinal cross-sectional view of the clip-illuminator shown in FIG. 3;

FIG. 5 is a fragmentary enlarged view of the remote battery pack shown in FIG. 3, with the front cover removed;

FIG. 6 is a side view of FIG. 5; and

FIG. 7 is a fragmentary view of FIG. 5 showing the power cord retracted.

Like parts are referred to by like reference characters throughout the figures of the drawings.

DETAILED DESCRIPTION

Referring first to the self-powered speculum holder-illuminator embodiment shown in FIGS. 1 and 2, it comprises an illuminated speculum holder 20 and a sterile disposable or reusable tubular speculum 22.

The speculum holder 20 has a handle 24 comprising a cylindrical case with battery compartment housing 26 containing a battery compartment 28, a switch housing 29 containing a switch compartment 30, and a cylindrical speculum support sleeve 31.

The case 26 is closed at the bottom and has an upper, open end with internal threads 25. A battery 36, preferably rechargeable, is in compartment 28. If desired, means in the form of a charging receptacle 45, shown in broken lines in FIG. 2, may be included to charge the battery in place from an external charger (not shown).

The switch housing 29 has a lower cylindrical skirt 23 with external threads 27, and an upper cylindrical neck 21, both joined by an intermediate annular wall 19. The neck is connected as by brazing or welding to the speculum support sleeve 31 which is at right angles to the switch housing 29. The lower end of skirt 23 is closed by means of a wall or disk 32 of electrical insulating material. This may be sealed by adhesive or a press fit into an open end bore 33. The battery housing 26 is detachably screw-threadedly engaged with the switch housing 29 by threads 25 and 27 for the purpose of removing or replacing battery 36.

Switch compartment 30 is thus completely sealed from battery compartment 28 by disk 32. An on/off switch 38 is located in the switch compartment and has an operating button 40 extending through the switch housing wall.

A first contact consisting of a spring 35 fastened to the battery side of disk 32 engages the top terminal of battery 36. The spring is fastened to the disk by a conductive rivet 37 which in turn is connected to one terminal of switch 38 by a first conductor 39. The other terminal of the switch is connected via a second conductor 41 to a lighting assembly 46 as will be described.

The speculum support sleeve 31 is open at both ends. The proximal end provides a viewing opening 64. A counterbore at the distal end provides a recess 66 for the speculum 22.

The tubular speculum 22 may be of any inexpensive, sterile, disposable or reusable material such as plastic or cardboard, preferably with a light-reflective inner surface and an external slick or lubricated coating of biologically safe material such as silicone or teflon. As shown in FIG. 2, the proximal end may be provided with an open-ended longitudinal slot 34. FIG. 2 also shows a pin 70 engageable with the slot 34 to hold the speculum tube in the recess 66. Alternatively, a plain end, non-slotted speculum tube may be used by removing the pin 70. An example is shown in U.S. Pat. No. 3,631,852 issued Jan. 4, 1972 on "Disposable Speculum For Animals".

A lighting assembly 46 comprises a permanent L-shaped base bulb holder unit 48 and a replaceable bulb housing unit 50. The bulb holder unit has opposite tubular leg members 52 and 54 disposed at substantially right angles to one another. These are suitably joined as by brazing or soldering. Vertical leg member 52 is snugly inserted in bore 56 formed in neck portion 21 and is held by a set screw 58 extending through the neck wall into engagement with a flat 60 formed on the back side of the leg member. This automatically orients the lighting assembly so leg 54 is parallel to the axis of speculum support sleeve 31. Horizontal leg member 54 has a screw socket 62 with internal threads 63 and a center contact 65 in an insulating bushing 61 which is telescopically slidable within bore 67. A spring 69 is compressibly interposed between the bushing 61 and shoulder 71 thereby urging the second contact 65 forwardly against third contact 72 in the bulb housing 50.

The bulb housing unit 50 is completely sealed and capable of being sterilized by standard procedures. It has a plug portion 73 consisting of external threads 74 and the above-described third contact 72. The latter is centrally located in insulating bushing 75. A high intensity bulb 76, preferably a sub-miniature halogen-cycle type, is contained within a bore 77 in the bulb housing unit 50. The particular bulb which is shown by way of illustration but not by way of limitation has an outer metallic liner 78 in grounding contact with the bulb housing unit 50. While a filament type bulb is shown, any other type may be employed so long as it produces a high light level when energized through third contact 72 and tubular casing 91. One side of lhe bulb is connected to the liner 78 and the other side is connected to the third contact 72 via a wire 79 extending through the bushing 75. At the forward (distal) end of the bulb housing unit, a threaded retaining ring 80 holds a protective front lens or window 82 against a sealing ring 81. Screw driver slots 83 in both the retaining ring 80 and housing 50 facilitate removal of the bulb housing for replacement or sterilization.

In normal operation, the bulb 76 will be energized, in response to closing switch 38, by a circuit including the top battery terminal, first contact (spring) 35, conductor 39, switch 38 conductor 41, second and third contacts 65 and 72, bulb 76, liner 78, and grounding connections through the lighting assembly 46, switch housing 29, battery housing 26 and pad 42 to the bottom battery terminal. Preferably, the spring 35 and pad 42 will be sized so the battery will function satisfactorily regardless of it being placed in a conventional right side up or upside down position.

Referring now to the light weight clip-illuminator embodiment of the invention shown in FIGS. 3 and 4, it comprises a base bulb holder unit 86 and a bulb housing unit similar to housing unit 50 already described. The bulb housing unit 50 may be used interchangeably with the bulb holder unit 86 shown in FIG. 4 and the bulb holder unit 48 shown in FIG. 2. Their socket portions are identical, making this interchangability possible.

The bulb holder unit 86 comprises a tubular body 88 with spring clip means 89 having an attachment band 90 fastened to the outside. The bulb holder unit 86 has a screw socket 62a similar to socket 62 shown in FIG. 2. It has internal threads 63a and a center contact 65a in an insulating bushing 61a which is longitudinally slidable within a bore 67a. A spring 69a is compressibly interposed between shoulder 71a and the movable bushing 61a, thereby urging the contact 65a outwardly into engagement with the contact 72 on the bulb housing 50. A two-conductor electrical cord 92 extends through a rubberlike cord protector 87 at the end of the bulb holder unit and terminates in a plug 98. One conductor 94 is connected to contact 65a. Another conductor 96 is grounded to the body 88.

As shown in FIGS. 3 and 4, the clip-illuminator 85 is temporarily fastened within the proximal end of a tubular speculum 22. The clip 89 may be fitted within the speculum slot 34 as shown in FIG. 4. The clip-illuminator 85, cord 92 and plug 98 comprises a unit which can be separately disinfected or sterilized. If the speculum is unslotted, the clip is simply hooked over the edge of the tube wall at the proximal end.

The clip-illuminator is energized by a remote battery power pack, preferably of very large capacity, enabling extended use without replacing or recharging the batteries. This is shown in FIGS. 5, 6 and 7. It comprises a casing 104 with a bottom opening 106 and a cover plate 108. A plurality of at least two batteries, which may be similar or identical to battery 36 described above, are connected in parallel with one another and have opposite terminals connected through an on/off switch 112, brushes 114, 114, and slip rings 116, 116 to a multiple conductor power cord 118 wound upon a reel 120 journaled for manual rotation by an external crank 122. A socket 124 at the end of cord 118 may be connected to plug 98 to energize the clip-illuminator.

The batteries 36 in the auxiliary power pack 102 will preferably be of the rechargeable type, and means may be provided for recharging them in place within the casing 104 in a conventional manner, from an external charger (not shown) through a charging receptacle 126 indicated in broken lines in FIGS. 5 and 6.

The power pack 102 is small enough to be readily portable and may be carried on a user's belt, as shown in FIG. 3, by means of a belt fastener 128 (FIG. 6).

The clip-illuminator 85 is compact, light weight and portable and makes possible a wide variety of veterinary procedures through the open tube 22 in addition to allowing observation of internal tissues.

In using the clip-illuminator, the operator will unreel the cord 118 by pulling it out of the casing 104 and connecting plug 98 into socket 124. When the examination or other procedure is completed, he can disconnect the plug 98 and socket 124 and wind the cord back into the casing by means of the crank 122. This will store the cord 118 and plug 124 in the casing as shown in FIG. 7. The switch 112 corresponds to the switch 38 in the self-powered embodiment shown in FIGS. 1 and 2. The operator energizes the clip-illuminator 85 by closing switch 112 on the belt supported battery power pack 102.

While particular examples of the present invention have been shown and described, it will be apparent that changes and modifications may be made without departing from the invention in its broadest aspect. For example, while the spring clip 89 is illustrated and described to hold the clip-illuminator 85 temporarily on a speculum tube, a wide variety of other clips and retainers may be utilized for this purpose. The terms "clip" and "clip means" where they appear in the claims therefore should be broadly construed. The aim of the intended claims is to cover all such changes and modifications included within the spirit and scope of the invention as recited in the appended claims.

The embodiments of the invention in which an exclusive property or privilege is claimed are defined as follows:

1. A large animal speculum holder and battery-powered illuminator for a tubular speculum comprising:
   a handle having a cylindrical case with separate battery and switch compartment housings at opposite end portions thereof;
   said switch compartment housing having a bore at one end;
   a wall separating said housings for effectively sealing the switch compartment from the battery compartment;
   first contact means supported on said wall engageable with a terminal of a battery in said battery compartment;
   switch means located in said switch compartment with actuator means externally of the handle;
   a speculum support sleeve open at both ends fastened across said switch compartment housing at substantially right angles thereto, the proximal end of said sleeve providing a viewing opening, and the distal end of said sleeve providing a recess for receiving a tubular speculum inserted therein;
   a lighting assembly comprising an L-shaped base bulb holder unit and a separable bulb housing unit;
   said base bulb holder unit having opposite tubular leg members disposed at substantially right angles to one another, means locking one of said leg members into said bore in the switch compartment housing with the other leg member extending parallel to the support sleeve toward the distal end thereof closely adjacent the wall of said support sleeve, said other leg member having socket means with a second contact therein;
   said bulb housing unit comprising a tubular member parallel to the axis of the speculum support sleeve having plug means at one end connectable to said socket means and having a third contact engageable with said second contact in said socket means, a bulb in the opposite end positioned to direct light toward the distal end of a tubular speculum inserted in said sleeve, and means including a lens sealing said bulb within said other leg member; and
   an electrical circuit for energizing said bulb in response to actuation of said switch means including conductor means interconnecting said first, second and third contacts with said switch means, and a return path completing the circuit through said lighting assembly and handle to the other terminal of the battery.

2. A large animal speculum holder and battery-powered illuminator according to claim 1 in which the light-emitting end of the bulb housing unit overlaps the proximal end of a tubular speculum inserted in the support sleeve for maximizing transfer of light to the distal end of the speculum.

3. A large animal speculum holder and battery-powered illuminator according to claim 1 in which said recess is a counterbore in the distal end portion of said speculum support sleeve.

4. A large animal speculum holder and battery-powered illuminator according to claim 1 in which a pin fastened to the support sleeve extends into the recess in position to engage a slot in the proximal end portion of a tubular speculum inserted therein.

5. A large animal speculum holder and battery-powered illuminator according to claim 1 in which the tubular member of the bulb housing unit comprises electrically conductive material and the plug means includes a threaded portion of the tubular member engageable with matching threads in the socket means, the third contact means is centrally located at the end of the plug means and electrically insulated from the tubular member, the bulb has opposite ends connected respectively with the third contact and with the tubular member, and the lens is removably held by a screw-threaded retaining ring at the distal end of the bulb housing unit to provide access to the bulb.

6. A large animal speculum holder and battery-powered illuminator according to claim 1 in which the means for locking said one of said leg members into the bore in the switch compartment housing comprises a set screw extending through a threaded opening in the wall of the switch compartment housing, and a matching surface on said one leg member engageable by said set screw to maintain said other leg member parallel to the axis of the support sleeve.

7. A bulb housing unit for a large animal speculum holder and illuminator which is optionally, interchangeably usable in a system employing alternate holder-illuminator embodiments which are powered by a self-contained battery or by a remote battery, said bulb housing unit comprising:
 a tubular member of electrically conductive material having plug means at the proximal end and a forwardly-open distal end;
 an insulating bushing in the proximal end portion of the tubular member;
 a central contact at the proximal end of the insulating bushing coaxial with respect to said plug means and electrically insulated from the tubular member;
 a bulb within said cavity positioned to direct light through the forwardly open distal end thereof;
 means including a lens at the distal end sealing said bulb within said tubular member; and
 electrical conductors within said tubular member connecting opposite sides of the bulb, to the central contact and the tubular member, respectively.

8. A large animal speculum holder and battery-powered illuminator consisting of a clip-illuminator adapted to be mounted temporarily within a tubular speculum during a veterinary procedure, said clip-illuminator comprising:
 an elongated base bulb holder unit having clip means for fastening it temporarily within the proximal end portion of a tubular speculum and having socket means at the distal end engageable with the plug means of a bulb housing unit made according to claim 7;
 a multi-conductor power cord extending from the proximal end of said base bulb holder unit to a remote battery pack;
 said base bulb holder unit providing connections between the conductors in said cord and said contact and tubular member in said bulb housing unit; and
 manually actuatable switch means for energizing the bulb in the bulb housing unit from said remote battery pack.

9. A large animal speculum and battery-powered illuminator according to claim 8 in which the remote battery pack comprises a battery carried in a portable casing having a reel with said power cord wound upon it, means including slip rings and brushes connecting the end of said power cord remote from the base bulb holder unit to the battery, said reel being rotatable in one direction to pay out cord for use with said speculum holder, and crank means for manually rotating the reel in the opposite direction to wind cord on the reel and store it within the casing when not in use.

10. A large animal speculum holder and battery-powered illuminator for a tubular speculum comprising:
 a clip-illuminator consisting of an elongated base bulb holder unit having clip means for fastening it temporarily within the proximal end portion of a tubular speculum and having a bulb housing unit removably attached thereto;
 a bulb at the distal end of said bulb housing unit positioned to direct light toward the distal end of the tubular speculum;
 a portable battery casing having external attachment means facilitating carrying by a user;
 a battery within said casing;
 a reel within said casing having a conductor cord wound thereon, said cord being connected at one end to the battery and at the other end to said base bulb holder unit; and
 crank means for said reel;
 whereby the reel may be rotated in one direction to pay out cord for use with said holder, and rotated in the opposite direction to wind cord onto the reel for storage within the casing when not in use.

11. A large animal speculum holder and battery-powered illuminator according to claim 10 in which:
 said clip means is adapted to extend through a slot in the wall of the tubular speculum and engage an outside surface thereof to hold the clip-illuminator stably within the speculum.

* * * * *